United States Patent [19]

Minchin et al.

[11] Patent Number: 5,118,690

[45] Date of Patent: Jun. 2, 1992

[54] PHARMACEUTICAL TETRAHYDROISOQUINOLINES

[75] Inventors: Michael C. W. Minchin, Oxford; Alan C. White, Englefield Green; John F. White, Wokingham, all of England

[73] Assignee: John Wyeth & Brother Limited, Maiden head, England

[21] Appl. No.: 780,372

[22] Filed: Oct. 21, 1991

Related U.S. Application Data

[63] Continuation of Ser. No. 584,216, Sep. 18, 1990, abandoned.

[30] Foreign Application Priority Data

Sep. 20, 1989 [GB] United Kingdom ............... 8921304

[51] Int. Cl.$^5$ ..................... A61K 31/47; C07D 41/00
[52] U.S. Cl. ..................... 514/314; 546/167
[58] Field of Search ............... 514/307, 314; 546/167

[56] References Cited

U.S. PATENT DOCUMENTS

| | | | |
|---|---|---|---|
| 4,622,329 | 11/1986 | Bernath et al. | 514/307 |
| 4,666,918 | 5/1987 | Ivanova et al. | 514/307 |

FOREIGN PATENT DOCUMENTS

| | | |
|---|---|---|
| 0842831 | 5/1970 | Canada. |
| 230871 | 8/1987 | European Pat. Off.. |
| 7039269 | 4/1988 | Japan. |
| 642286 | 8/1950 | United Kingdom. |
| 1062899 | 3/1967 | United Kingdom. |
| 1070308 | 6/1967 | United Kingdom. |
| 1173687 | 12/1969 | United Kingdom. |
| 1174385 | 12/1969 | United Kingdom. |
| 1470675 | 4/1977 | United Kingdom. |
| 2213482 | 8/1989 | United Kingdom. |

OTHER PUBLICATIONS

Yamoto et al, *Yakugaki Zasshi* 87(9):1083–1088, 1967, Synthesis of 6,7-dihydroxy-1,2,3,4-tetrahydroisoquinoline derivatives.
Sheykova & Nikolova. *Bull. Inst. Physiol.* VII: 243–252, 1964, Pharmacological activity of some analogs of papaverine, II. Communication. [see also *Chem Abstracts* 62:16784, 1965.]
Gray et al, *J. Med. Chem.* 32(6): 1242–1248. Phencyclidine-like effects of tetrahydroisoquinolines & related compounds.
Inwegen et al. *Biochem. Pharmacol.* 28:1307–1312, 1979, Dihydro- & tetrahydroisoquinolines as inhibitors of cyclic nucleotide phosphodiesterases from dog heart.
Translation of —Yakugaku Zasshi 83:1048 (1963).
Jap. J. Pharmacol. 17, 143 (1967), Yoshio Iwasawa et al.
J. Heterocycl. Chem. 4(4) 469 (1967), Wilhelm Wenner et al.
*C. A. 68:10492g, Bisaku Yamato et al.
C.A. 72:66846.
C.A. 69:106,573d.
C.A. 73:25266m, Seeger et al.
Chem. Ber. 103:1674 (1970).
C.A. 79:834296, Kigazawa et al.
C.A. 82:4441k, Shamma M.
C.A. 100:22956b, Piper Ian M. et al.
C.A. 100:34749z.
J. Chem. Soc. Perkins Trans I 1985(2), 275, Barker et al.
C.A. 30:8224(6).
C.A. 49:5495b.
Iav. Inst. Fiziol. Bulgar Akad Nauk 7:243 (1964)—plus translation C.A. 62:16873h.
J. Chem. Soc. 1955, 430.
Agr. Biol. Chem. 39(2):547 (1975) Morita et al.
Eur. J. Pharmacol. 82:131 (1982), Pearce et al.
Nature 280:514 (1979).
Neuropharmacol 27(10) 1003 (1988), Ennis et al.
Neuropharmacol: 25(2) 175 (1985). Rastogi et al.
C.A. 52:15596h.
(C.A. 74:141571b)—See Japanese Patent above (1983).
C.A. 59:7553.
C.A. 60:10732h (Yakugaku Zasshi 53:1048 (1963)).
C.A. 58:11327g.

*Primary Examiner*—S. J. Friedman
*Attorney, Agent, or Firm*—Arnold S. Milowsky

[57] ABSTRACT

The invention concerns a method for treating pain and/or CNS disorders characterized in that the method uses a compound which acts selectively as an antagonist of gamma aminobutyric acid (GABA) at GABA autoreceptors relative to GABA$_A$ receptors.

33 Claims, No Drawings

PHARMACEUTICAL TETRAHYDROISOQUINOLINES

This application is a continuation of application Ser. No. 07/584,216 filed Sep. 18, 1990 now abandoned.

This invention relates to use of a new pharmacological activity and to heterocyclic compounds possessing said pharmacological activity, to processes for preparing them and to pharmaceutical compositions containing them. More particularly this invention relates to the treatment or prevention of various disorders utilizing a new pharmacological activity operating via a new class of GABA receptor (GABA = gamma aminobutyric acid).

GABA is one of the most widespread and abundant transmitters in the mammalian central nervous system and plays a major role in the control of brain excitability. It is similarly implicated in the benzodiazepine-mediated relief of anxiety.

At present three GABA receptors have been identified in the central nervous system (CNS). These are (1) a $GABA_A$- receptor known to be mainly postsynaptic and mediating neuronal inhibition—see for example Stephenson, F. A. Biochem, J., 249 pp 21-32 (1988); (2) a $GABA_B$ receptor located presynaptically and mediating the inhibition of release of a number of neuro-transmitters, eg. noradrenaline and aspartic acid, but not GABA—see for example Bowery, N. G. et al , Nature, 283, 92-94 (1980); and (3) a GABA autoreceptor which modulates the release of GABA from neurones—see for example Mitchell, P. R., and Martin, I. L. Nature, 274 904-905(1978); Arbilla, S. Kanal, J. L and Langer, S. Z. Eur.J.Pharmac., 57, 211-217 (1979) and Brennan M. J. W. et al, Molec. Pharmac., 19, 27-30 (1981).

The pharmacological importance of these receptors is currently a subject of investigation with a major part of the work involving the search for anticonvulsant drugs with a mode of action involving $GABA_A$ receptors.

The GABA autoreceptor is capable of regulating the release of GABA from GABAergic neurons which means an agonist at the autoreceptor would decrease the GABA release hence decreasing GABA function. By contrast, an antagonist at the GABA autoreceptor would block the action of agonist, including the natural agonist GABA, and hence increase GABA function.

Previously the autoreceptor was believed to have the same pharmacology as the $GABA_A$ site—see Molec. Pharm, 19, 27-30 (1981) However, we now have evidence that the GABA autoreceptor is a distinct pharmacological entity and we have invented compounds that have selective actions at the GABA autoreceptor, ie. they do not act, or have only weak action, on $GABA_A$ receptors; e.g a selectivity of tenfold or greater.

In the methods of this invention it is preferred that the compound having GABA autoreceptor antagonist activity is selective in that it has little or no activity at $GABA_A$ receptors, e.g. selectivity of 100 or more preferably 1000 or greater.

Accordingly in one aspect this invention provides a compound for use in analgesia or treating or preventing CNS disorders such as those requiring anxiolytic, hypnotic, muscle relaxant, anticonvulsant, antidepressant, antipsychotic and/or movement disorder therapy characterised in that the compound has selective antagonist activity at GABA autoreceptors. The invention also provides a pharmaceutical composition comprising a compound having selective antagonist activity at GABA autoreceptors.

Examples of general disorders which can be treated by selective GABA autoreceptor antagonists are anxiety (eg. generalised anxiety disorder), agoraphobia, epilepsy, muscular spasm, sleep disorders and dyskinesias.

This invention also provides a method of treating or preventing pain and/or CNS disorders such as those requiring anxiolytic, hypnotic, muscle relaxant, anticonvulsant, antidepressant, antipsychotic and/or movement disorder therapy which comprises administering an effective amount of a compound having selective antagonist activity at GABA autoreceptors.

We have found one class of compound that possesses GABA autoreceptor antagonist activity has the general formula:

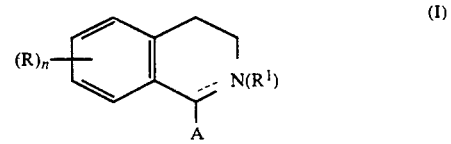

where the dotted line represents an optional bond, which when absent means the $R^1$ group is present and vice versa;

$(R)_n$ represent optional substitution on the benzene ring in one or more of the vacant ring positions by one or more substituents the same or different selected from lower alkyl, lower alkoxy, halogen, hydroxy, nitro, carboxy, lower alkylthio, SH, $NH_2$, or mono- or diloweralkylamino or $(R)_n$ represents disubstitution by an alkylenedioxy radical, eg. methylene-, ethylenedioxy); $R^1$ when present represents hydrogen, lower alkyl, aryl, aryl lower alkyl; the aryl and aryl lower alkyl groups being optionally substituted by one or more substituents the same or different selected from hydroxy, halogen, lower alkyl, lower alkoxy, $NO_2$, CN, carboxy, lower alkylthio, SH, $NH_2$ and mono- or diloweralkylamino or by alkylenedioxy, $R^2$ represents hydrogen or lower alkyl; and A represents aryl optionally substituted by one or more substituents as defined for $R^1$ when aryl; or a group of formula

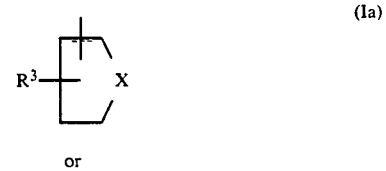

or

wherein the dotted lines represent optional bonds, X represents NH, oxygen or sulphur and $R^3$ represents hydrogen or lower alkyl; or a pharmaceutically acceptable salt thereof.

This invention provides novel compounds of formula I including those where A represents formula Ia or Ic and the use of compounds of formula I in the preparation of medicaments for the treatment of CNS disorders.

The compounds of formula I may possess one or more asymmetric centres and accordingly the compounds may exist and be isolated in a number of optically active stereoisomeric forms. This invention encompasses the compounds of formula I in any optically active form or mixtures thereof eg, racemates or diastereoisomers. Standard separation techniques may be used to isolate particular enantiomeric and diastereomeric forms. For example a racemic mixture may be converted to a mixture of optically active diastereoisomers by reaction with a single enantiomer of a resolving agent (for example by salt formation or fomation of a covalent bond). The resulting mixture of optically active diastereoisomers may be separated by standard techniques (e.g. crystallisation or chromatography) and individual optically active diastereoisomers then treated to remove the resolving agent thereby releasing the single enantiomer of the compound of the invention. Chiral chromatography (using a chiral support, eluent or ion pairing agent) may also be used to separate enantiomeric mixtures directly.

Stereospecific synthesis using optically active starting materials and/or chiral reagent catalyst and/or solvents may also be employed to prepare particular diastereoisomers or even a particular enantiomer.

For example where the compound of formula I is prepared by an addition process creating one or more optical centres then carrying out the reaction using a chiral catalyst or agent or in a chiral environment can give the product as a single enantiomer.

Tetrahydroisoquinolines of formula I have at least one asymmetric centre at the 1- position. Accordingly such compounds can be isolated as the R- or S- enantiomers. When A has formula Ia or Ic and the bond linking A to the 1- position is to a saturated carbon in A (e.g when A is 2-tetrahydrofuranyl, 3-tetrahydrofuranyl, 2-tetrahydrothienyl etc.,) then two centres are present and the compounds can be isolated as the individual R,S-, S,R-, R,R- and S,S- enantiomers. All such enantiomers of the compounds of formula I are included in this invention.

By the term "lower" is meant a group containing 1 to 6 carbon atoms, preferably 1 to 4.

Examples of lower alkyl groups for each of $(R)_n$, $R^2$ and $R^3$ and as a substituent on the aryl or aryl lower alkyl $R^1$ group are methyl, ethyl, n-propyl, isopropyl and n-butyl. Examples of lower alkoxy groups for $(R)_n$, and as a substituent on the aryl or aryl lower alkyl $R^1$ group are methoxy, ethoxy, n-propoxy and n-butoxy The term aryl means any carbocyclic or heterocyclic group having aromatic character, the heteroatom or -atoms when present being selected from oxygen, nitrogen and sulphur. Carbocyclic aryl groups having 6 to 10 carbon atoms eg. phenyl or naphthyl and heterocyclic aryl groups of 5 to 10 ring atoms are preferred, eg. pyridyl, furyl, thienyl, thiazolyl.

Examples of $R^1$ are hydrogen, methyl, ethyl, propyl, benzyl, substituted benzyl such as halobenzyl, eg. chlorobenzyl, bromobenzyl.

Examples of $(R)_n$ when other than hydrogen are methyl, ethyl, propyl, methoxy, ethoxy, propoxy, chloro, bromo, fluoro or combinations thereof at one or more of the vacant 4,5,6 or 7 ring positions eg. 6,7-dimethyl; 6,7-dimethoxy; 6,7-methylenedioxy 6,7-ethylenedioxy.

Examples of A are phenyl, pyrid-2-yl, 2-furanyl, 2,3-dihydrofuran-5-yl, 2-tetrahydrofuranyl, 2-thienyl, 2-tetrahydrothienyl, 2-pyranyl and 2-tetrahydropyranyl and such groups substituted by methyl. Preferred substituents for phenyl are electron donating groups such as hydroxy; amino and mono- or dialkyl-amino, lower alkoxy, lower alkylthio and mercapto. The compounds of formula I form salts with organic and inorganic acids. Examples of such salts are those formed with one of the following acids: hydrochloric, hydrobromic, hydroiodic, sulphuric, phosphoric, nitric, acetic, citric, tartaric, fumaric, succinic, malonic, formic, maleic, oxalic and organosulphonic acid such as methanesulphonic and tosylic acid. Quaternary salts may also be formed when $R^1$ is other than hydrogen or when $R^1$ is absent by alkylation e.g using an alkyl or aralkyl halide. Preferred, compounds of the invention have the formula:

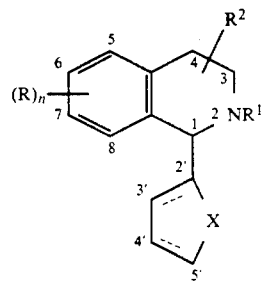

where the dotted lines represent optional bonds and $R^1$ is as defined above.

Compounds have previously been shown to be antagonists at the GABA autoreceptor, for example, picrotoxin and bicuculline (known convulsants) but such compounds are non-selective in that they are also active at the $GABA_A$ receptor.

Compounds showing selective properties at the GABA autoreceptor are desirable since additional antagonist activity at the $GABA_A$ receptor would cause many side effects such as convulsions.

The compounds of formula I demonstrate pharmaceutical activity at GABA autoreceptors, more specifically they demonstrate antagonist activity as shown by standard in vitro test procedures. Advantageously compounds of formula I appear to be selective in that they display little or no activity at $GABA_A$ receptors. The following test procedures were used to measure antagonist activity at (a) GABA autoreceptors by blockade of agonist-induced inhibition of potassium-evoked GABA release from rat cortex in vitro (Procedure 1); and (b) $GABA_A$ receptors by antagonism of agonist-induced depolarization of the isolated rat vagus nerve (Procedure 2):

Procedure (1)

Slices (0.25×0.25×2.0 mm) of rat cerebral cortex are prepared using a McIlwain tissue chopper. The slices are incubated in Krebs-Henseleit solution containing [$^3$H]-GABA ($10^{-7}$M) in the presence of amino-oxyacetic acid (AOAA) for 20 minutes at 37° C., rinsed with 5ml aliquots of Krebs-Henseleit solution and transferred to 10 superfusion chambers (volume 300μl). The slices are continuously superfused with Krebs-Henseleit solution (0.4 ml min$^{-1}$) containing AOAA ($10^{-5}$M) and fractions of the superfusate collected every 4 minutes. Transmitter release is induced by 4 minute exposure to a Krebs-Henseleit solution containing 25 mM potassium ion (with concomitant reduction in sodium to maintain osmolarity) after 68 ($S_2$) and 92 ($S_2$) minutes of superfusion. The antagonist compound under study is added to the superfusing medium 10 minutes prior to the first its ability to shift this concentration-response curve to the right.

In the aforementioned tests the following representative compounds gave the results shown.

Compound

![structure]

Where:

| Compound | Configuration | $R^{10}$ | $R^{11}$ | $R^1$ | A | Antagonism at GABA autoreceptor $pA_2$ values |
|---|---|---|---|---|---|---|
| A | 1RS,2'SR | MeO— | MeO— | H | tetrahydrofuran-2-yl | 7.0 a) |
| B | 1RS,2'RS | MeO— | MeO— | H | " | 5.2 |
| C | 1RS,2'SR | H | H | H | " | 8.5 |
| D | 1RS,2'SR | H | H | Me | " | 9.2 b) |
| E | 1RS | H | H | H | thien-2-yl | 8.4 | a) Compound was inactive at $10^{-4}$ M in the procedure measuring antagonism at $GABA_A$ receptors
b) Compound was inactive at $10^{-5}$ M in the procedure measuring antagonism at $GABA_A$ receptors potassium stimulation and remains throughout the superfusion. The GABA autoreceptor is activated by adding the agonist muscimol 20 minutes before the second potassium stimulation. The residual radioactivity in the slices at the end of the experiment together with that in the superfusate. fractions is measured by liquid scintillation counting Calculations: The amount of radioactivity in each fraction is expressed as a percentage of the total radioactivity in the tissue at the start of the respective collection period. The amount of radioactivity released above basal by the increased potassium is calculated and the ratio S2/S1 obtained. The S2/S1 ratio from muscimol-treated slices is expressed as a percentage of the control drug-free S2/S1 ratio. A dose-response curve for the agonist muscimol is constructed and the effect of antagonists is measured by their ability to displace this dose-response curve to the right. From this measurement a $pA_2$ value can be calculated. Alternatively, an $IC_{50}$ value for antagonists can be calculated by inhibiting the effect of a single concentration of muscimol with increasing concentrations of antagonist.

Procedure (2)

Male Sprague-Dawley rats (250–400g) are killed by a blow to the head and cervical dislocation. The cervical vagus nerves are transferred into Krebs' solution at room temperature and the connective tissue sheath removed. The vagus nerves are placed in two-compartment Perspex baths to permit extracellular recording of agonist induced depolarizations. Each nerve projects from one compartment to the next by way of a grease filled slot, the grease serving to insulate the compartments from each other. The d.c. potential between the compartments is recorded using silver-silver chloride electrodes in saline-agar bridges and displayed on a Grass polygraph. One compartment is continuously perfused (5ml $min^{-1}$) with Krebs' solution at 27° C. to which agonist and antagonist drugs are added. The second compartment remains filled with Krebs' solution alone. Non-cumulative concentration-response curves to GABA ($10^{-6}$ to $3 \times 10^{-4}$M) are obtained using a 5 min contact time and 10–20 min wash period and the effect of the test antagonist compound is measured by The (−) enantiomer of Compound C as the maleate salt had an $IC_{50}$ value of 0.02 μM; whereas the (+) isomer maleate salt had an $IC_{50}$ of 8.6 μM. The (+) isomer of Compound D in the form of the oxalate salt had an $IC_{50}$ value of 0.0027 μM whereas the (−) isomer had an $IC_{50}$ of 0.26 μM.

This invention also provides processes for preparing the compounds of formula I or salts thereof.

Compounds of formula (I) may be prepared by one of the following processes:

(a) cyclising a compound of formula (II)

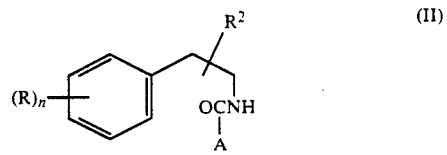

in the presence of a Lewis Acid, wherein $(R)_n$, $R^2$ and A are as defined above to give a dihydro compound of formula I wherein the optional bond is present and $R^1$ is absent);

or (b) reducing a compound of formula I wherein the optional bond is present having formula Id shown below

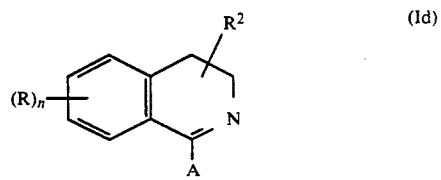

or a quaternery salt thereof to give a compound of formula I wherein $R^1$ is hydrogen and the optional bond is absent;

or (c) reacting a compound of formula (III)

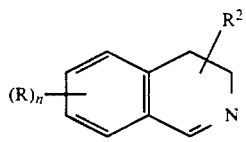

wherein $(R)_n$ and $R^2$ are as defined above, with trimethylsilyl triflate $(CF_3SO_3 Si(Me)_3)$ followed by an organo metallic compound of formula A—M where M is lithium, sodium, potassium, Mg-hal (where hal is a halogen such as chlorine or bromine) and A is as defined above providing that where necessary A contains a protecting group and if required this group or feature is removed as the last step of the reaction;

or (d) reductive amination a compound of formula I wherein $R^1$ is hydrogen (and the optional bond is absent) with an aldehyde of formula $R^4CHO$ wherein $R^4$ is hydrogen, $C_1-C_5$ alkyl or optionally substituted arylalkyl where the alkyl group is $C_1-C_5$ and the substituents are as defined in connection with the aryl $R^1$ group; to give a compound of formula I wherein $R^1$ is lower alkyl or optionally substituted aryl lower alkyl as hereinbefore defined;

or (e) reducing a compound of formula (IV)

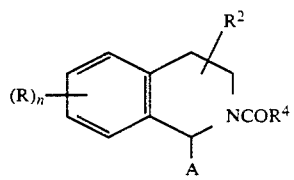

where $A, OR)_n$, $R^2$ are as hereinbefore defined and $R^4$ is as defined above or optionally substituted aroyl to give a compound of formula I where in $R^1$ is lower alkyl or optionally substituted aryl lower alkyl as hereinbefore defined;

or (f) reducing a compound of formula I wherein A contains one or more double bonds (e.g. furyl, or dihydrofuryl) to give a compound of formula I where in A is a saturated molecule (e.g.tetrahydrofuryl).

or (g) acidifying a basic compound of formula I to give an acid addition salt or neutralising an acid addition salt to give a compound of formula I, or (h) alkylating a compound of formula I wherein $R^1$ is not present or $R^1$ is other than hydrogen to give a quaternary ammonium salt or (i) separating an isomeric mixture of a compound of formula I to give an optically active form, or (j) reacting a phenethylamine compound of formula

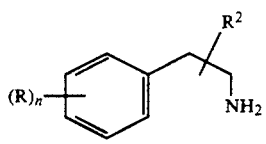

wherein $R^2$ is as defined above and $(R)_n$ represents hydrogen, alkylenedioxy or one or more substituents selected from halogen, lower alkyl, OH, SH, lower alkoxy, lower alkythio, amino and mono- or di-loweralkylamino, with an aldehyde of formula ACHO wherein A is as hereinbefore described to give a corresponding tetrahydroisoquinoline of formula I.

Process (a) is conveniently carried out according to conditions suitable for carrying out the Bischler-Napieralski Reaction by mixing the compound of formula II with a Lewis acid such as phosphorus oxychloride, polyphosphoric acid or zinc chloride if desired in an inert solvent such as acetonitrile, with heating if required, followed by neutralisation. See for example Organic Reactions, Coll. Vol. VI 1951 (Wiley Publications) Chapter 2 p74 ff which describes the preparation of 3,4-dihydroisoquinolines by the Bischler-Napieralski Reaction.

The starting material of formula II used in process (a) may be prepared by acylation of a corresponding phenethylamine derivative of formula V

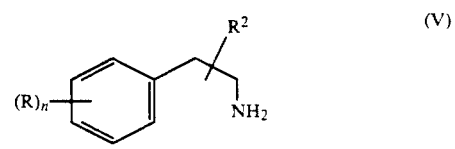

wherein $(R)_n$ and $R^2$ are as defined above using an acylating agent such as the acid chloride derived (e.g. using $PCl_5$, $SOCl_2$) from an acid of formula ACOOH where A is as defined as above.

Process (b) may be carried out by reduction of the compound of formula (Ia) using catalytic hydrogenation, with a suitable catalyst, e.g. palladium, at pressures of 1 to 4 atmospheres. The reduction may also be performed using a suitable selective complex metal hydride, e.g. an alkalimetal hydride such as $NaBH_4$. It is possible by use of a selective reducing agent e.g. ALPINE-BORANE (Registered Trade Mark) to obtain an excess of one enantiomer (optical isomer) of a ccompound of formula I. Where applicable (2 optical centres) an excess of the appropriate diastereoisomer can be obtained by modifying reduction conditions, e.g. by using a sterically demanding reducing group.

Process (c) may be conveniently carried out by first adding commercially avialable trimethylsilyl triflate to the compound of formula III at a low temperature e.g. from $-80°$ to $0°$ C. in an inert ethereal solvent, followed by addition at low temperature (e.g. $-80°$ to $0°$ C.) of the compound of formula A—M also in an inert ethereal solvent. Examples of A—M include the 2-lithium derivatives of furan, thiophene and dihydrofuran.

In order to obtain a desired A group in the compound of formula I it may be necessary to form a protected organo metallic compound of formula A—M. For example when X is NH in the A group this can be protected in the form $N-Si(alkyl)_3$ so that the metallic derivative of A can be prepared and reacted, followed by removal of the trialkylsilyl protecting group. Where it is desired to prepare an A group such as tetrahydrofuryl then the reaction may be carried out using the dihydrofuryl metal derivative (equivalent to a protected form) followed by reduction of the product to give the tetrahydrofuryl compound e.g. using process (f) above.

The starting material of formula III may be prepared by reacting a phenethylamine of formula V with formic acid/acetic anhydride and cyclising the product using the Bischler-Napieralski reaction.

Other starting materials used in the processes described herein are known compounds or can be prepared by methods analogous to those for preparing known compounds.

Process (f may be carried out by known methods for hydrogenating double bonds e.g. using Pt, Pd or Ni catalyst at 1-4 atmospheres.

Process (j) may be carried out using the Pictet-Spengler reaction.

Intermediates of formula VI

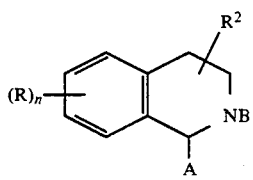 (VI)

used in processes above, wherein $(R)_n$, $R^2$ and A are as hereinbefore defined and B is —$COR^4$ wherein $R^4$ is as defined above are also within the scope of this invention.

As shown above compounds of formula I wherein the optional bond is present (and $R^1$ is absent) are intermediates to compounds of formula I where $R^1$ is hydrogen.

This invention also provides pharmaceutical compositions conprising a compound of formula I or a pharmaceutically acceptable salt thereof and a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term composition is intended to include the formulation of an active ingredient with encapsulating material as carrier, to give a capsule in which the active ingredient (with or without other carrier) is surrounded by carriers, which is thus in association with it. Similarly cachets are included.

Sterile liquid form compositions include sterile solutions, suspensions, emulsions, syrups, and elixirs.

The active ingredient can be dissolved or suspended in a pharmaceutically acceptable carrier, such a sterile water, sterile organic solvent or a mixture of both.

The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil The composition may be administered orally, nasally, rectally or parenterally.

Preferably the pharmaceutical composition is in unit dosage form, the composition is sub-divided in usit doses containing appropriate quantities of the active ingredient; the unit dosage form can be a packaged composition, the package containing specific quantities of compositions, for example packeted powders of vials or ampoules. The unit dosage form can be a capsule, cachet or tablet itself, or it can be the appropriate number of any of these in packaged form. The quantity of active ingredient in a unit dose of composition may be varied or adjusted from 1 to 500 mg or more, e.g. 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound.

For certain of the abovementioned conditions it is clear that the compounds may be used prophylactically as well as for the alleviation of acute symptoms. References herein to treatment or the like are to be understood to include such prophylactic treatment, as well as treatment of the acute conditions.

The following Examples illustrate the invention and methods for preparing compounds of the invention. In the Examples relative configurations of optical centres are denoted using the R,S notation. As used herein 1RS,2'SR means a racemic mixture of the 1R, 2'S and 1S, 2'R enantiomers.

EXAMPLE 1

1RS,2'SR-1-(2-Tetrahydrofuranyl)-1,2,3,4-tetrahydro-6,7 dimethoxyisoquinoline (a) A solution of 120g polyphosphoric acid ethyl ester (PPE) in chloroform (100ml) was stirred and heated to reflux as a solution of N-(3,4-dimethoxyphenethyl)tetrahydrofuran-2-carboxamide (14.33g) in chloroform (50ml) dropwise over ¼ hour. When addition was complete, relux was maintained for a further 5½ hours. After cooling, the mixture was poured cautiously onto a solution of $Na_2CO_3$ (100g) in water (1L). The mixture was stirred for 3 hours, then the layers were separated and the organic phase was washed with water and dried ($MgSO_4$) Filtration and evaporation gave a dark oil (21.2g) containing 1-(2-tetrahydrofuranyl)-3,4-dihydro-6,7-dimethoxyisoquinoline.

(b) The oil was dissolved in ethanol (250ml) and treated with $NaBH_4$ (6.0g). The mixture was stirred and heated under reflux for 3 hours, cooled, the solvents evaporated and the residue taken up in water. The aqueous mixture was extracted with dichloromethane (2×50 ml), the combined extracts washed with water and dried ($MgSO_4$). Filtration and evaporation gave a redbrown syrup (9.56g).

Preliminary chromatography on silica eluted with ethyl acetate, then 5% ethanol/ethyl acetate, gave the main product as a fraction of 4.24g. Further chromatography on neutral alumina eluted with toluene, then 5% ethyl acetate/toluene gave 2.74g of the principal product, an oil, apparently comprising two isomers (total 72%; glc), and other impurities.

The oil was dissolved in hot ethanol (5ml) and treated with oxalic acid (0.90g; 1 equiv.). The crystals which separated were collected by filtration, washed with cold ethanol and ether, then dried at 50°/1 mm, to give the title compound as the 1:1 ethanedioate salt (2.15g), mp. 203°-4° (dec).

Analysis: $C_{15}H_{21}NO_3$ $(COOH)_2$ requires C,57.8; H,6.6; N,4.0. Found: C,57.6; H,6.6; N,3.5%.

EXAMPLE 2

1RS,2'RS-1-(2-Tetrahydrofuranyl) -1,2,3,4- Tetrahydro -6, 7- dimethoxyisoquinoline 1-(2-(Tetrahydrofuryl) -3,4-dihydro -6,7- dimethoxyisoquinoline (26.67g) was reduced using sodium borohydride (7.5g) in ethanol (200ml) to give, after 4 hours at reflux and aqueous work-up and extraction, a brown-red oil (25.0g). Chromatography on silica eluted with 2% triethylamine -2-5% ethanol - toluene gave the product of Example 1 (19.78g). Further elution with 2% triethylamine -10% ethanol - toluene gave an oil (3.45g) which was further purified by chromatography on silica eluted with 2% triethylamine -5% ethanol-toluene to give the title compound 2.6g as an oil. The oil was purified further by dissolving 2.19g of the oil in hot ethanol and adding maleic acid (0.96g). After evaporating the solvent the residual was crystallised from isopropanol, then recrystallised from ethanol to give the 1:1 maleic acid salt of the title compound (1.74g) m.p. 160.5°-162.5° C. (dec).

Analysis: $C_{15}H_{21}NO_3C_4H_4O_4$ requires: C, 60.2; H, 6.6; N 3.7. Found: C, 60.0; H, 6.7; N, 3.7%

EXAMPLE 3

1RS, 2'SR-1-(2-Tetrahydrofuranyl)-1,2,3,4-Tetrahydro-2-Methyl-6,7-Dimethoxyisoquinoline A solution of compound of Example 1 as the free base (2.14g:8.12 mmol) in ethanol (50ml) was treated with 37% aqueous formalin solution (5ml; large excess) and 5% palladium on carbon (0.25g). The mixture was hydrogenated at atmospheric pressure for 3 hours when the theoretical amount of hydrogen had been taken up. The mixture was filtered through kieselguhr to give a pale yellow filtrate which was evaporated to give an oil (2.3g).

The oil was dissolved in hot ethanol (10ml) and acidified with maleic acid (0.96g; 1mol). The solvent was evaporated and the residual oil crystallised from acetonitrile-ether. Recrystallisation from isopropanol-ether gave the title compound as the maleic acid salt (1.65g) m.p. 147°-149°.

Analysis: $C_4H_4O_4$ requires: C, 61.1; H, 6.9; N, 3.6. Found C, 61.0; H, 7.1; N, 3.8%.

EXAMPLE 4

1RS, 2'SR-2-Benzyl-6,7-dimethoxy-1-(2-tetrahydrofuranyl)-1,2,3,4-tetrahydroisoquinoline a) An ice cooled solution of the compound of Example 1 (2.1g; 8.13mmol) and diisopropylethylamine (1.5ml, 1.11g) in dichloromethane (30ml) was treated dropwise with a solution of benzoyl chloride (0.95ml, 1.15g; 8.11mmol) in dichloromethane (30ml). When addition was complete, the clear solution was kept at room temperature for 2 hours, washed with water, dil.aq.$H_2SO_4$ water and aq. $Na_2CO_3$, then dried (MgSO4) Filtration and evaporation gave 1RS, 2'SR-2-benzoyl-6,7 -dimethoxy-1-(2-tetrahydrofuranyl) -1,2,3,4-isoquinoline (3.0g) as a yellow wax.

b) A solution of the product of step (a) (3.0g; 8.1mmol) in dry tetrahydrofuran (25ml) was added to a stirred solution of LiAlH4 (1.1g, 29mmol) in dry tetrahydrofuran (25ml) under nitrogen. When addition was complete, the mixture was stirred and heated to reflux for 8 hours, cooled and decomposed by the dropwise addition of water (1.1ml) 15% aq. NaOH 1.1ml) and water (3.3ml). After filtration, evaporation gave a yellow oil (2.83g).

The oil was chromatographed on silica eluted with 2% ethanol-2% triethylamine in toluene, and the main component was eluted rapidly as a yellow band. Evaporation of fractions containing product gave a yellow oil (1.85g), which was dissolved in hot isopropanol (5ml), treated with one molar equivalent of oxalic acid dihydrate and cooled. The crystals which separated were collected by filtration, washed well with isopropanol, then ether and dried at 4.0°/1mm, to give the title compound as the 1:1 ethanedioate salt (1.57g)mp 163°-166° C.

Analysis $C_{22}H_{27}NO_3$. $(COOH)_2$ requires: C,65.0;H,6.6;N,3.2. Found: C,65.0;H,7.0;N,3.2%

EXAMPLE 5

1RS, 2'SR-2-(4-Chlorobenzyl)-1-(2-tetrahydrofuran-yl) -1,2,3,4-tetrahydro-6,7-dimethoxyisoquinoline a) 1RS, 2'SR-2-(4-Chlorobenzoyl)-1-(2-tetrahydrofuran yl)-1,2,3,4-tetrahydro-6,7-dimethoxyisoquinoline was prepared by condensation of the compound of Example 1 and 4-chlorobenzoyl chloride in $CH_2Cl_2$ with diisopropylethylamine as the catalyst.

b) A solution of the product of step (a) (2.2g) in dry tetrahydrofuran (25ml) was added dropwise to an ice-cooled solution of 1.0m BH3 in tetrahydrofuran (80ml; large excess). When the addition was complete, the mixture was stirred and heated to reflux under a nitrogen blanket for 3½ hours. After cooling, the mixture was decomposed by dropwise addition of water (10ml), acetic acid (5ml; stirred for 1h), then dil. aq. NaOH in 50ml water; stirred for ¾h). The organic solvent was evaporated in vacuo and the aqueous residue was diluted with water (50ml) and extracted with dichloromethane (3×25ml). The combined organic extracts were dried (MgSO4), filtered and evaporated to give a gum (2.20g). This was purified by chromatography on silica diluted with 2% $Et_3N$-2% EtOH-toluene to give an oil (1.87g). The oil was dissolved in hot isopropanol (5ml), treated with one molar equivalent of oxalic acid dihydrate (0.61g) and cooled. The crystals which slowly separated were collected by filtration (0.97g) and recrystallised 3 times from ethanol to give the title compound (0.15g)mp 183-185° C.

Analysis: $C_{13}H_{17}NO_3$. $C_2H_2O_4$ requires: C, 61.4; H, 6.5; N, 4.8%. Found: C,61.4; H, 6.6; N, 4.7%.

EXAMPLE 6

1-(2-Furanyl)-1,2,3,4,-tetrahydro-6,7-dimeth isoquinoline a) (i) A solution of 1.5m $Li^nBu$ in hexane (13.4ml) was added dropwise to a solution of furan (1.45ml; 0.02mol) in dry tetrahydrofuran (10ml) at −78° under nitrogen. The mixture was stirred at −78° for 40minutes then 0° for 0.5h. Finally the mixture was diluted with THF (10ml).

(ii) Simultaneously with step (i), a solution of 6,7-dimethoxytetrahydroisoquinoline (3.82g, 0.02ml) in dry THF (40ml) was cooled to 0° C., then treated in dropwise with trimethylsilyltriflate (4.25ml; 0.022mol). (Ref: Synthetic Communications, 18(9), 893-8 (1988))

b) The mixture from step a(ii) was cooled to −78° C. as the solution from step a(i) was injected by nitrogen pressure directly from its flask. The mixture was stirred at −78° for 0.5 hours, then warmed to 0° with stirring for 3 hours.

Water (50ml) was stirred in, and the organic solvents were evaporated in vacuo. The aqueous residue was basified with aq. $Na_2CO_3$, extracted with dichloromethane (3×25ml) and the combined extracts dried ($MgSO_4$).

Filtration and evaporation gave a dark syrup (5.51g) which was flash-chromatographed twice on silica eluted with toluene and 2% ethanol-toluene. Evaporation of product fractions gave an oil (2.1g), which was treated with one equivalent of maleic acid in hot isopropanol. The solution turned red, and crystals formed on standing overnight. The lumps were powdered and recrystallised from isopropanol, to give the title compound as the 1:1 maleic acid salt (0.62g) mp 138°–140° C. (dec).

Analysis: $C_{15}H_{17}NO_3 \cdot C_4H_4O_4$ requires: C, 60.8; H, 5.6; N, 3.7. Found: C, 60.8; H, 5.7; N, 3.7%.

EXAMPLE 7

1-(2-Furanyl)-1,2,3,4-tetrahydroisoquinoline a) (i) 1.5M Li$^n$Bu in hexane (27ml; 0.04mol) was added dropwise to a solution of anhydrous furan (2.90ml; 0.04mol) in dry tetrahydrofuran (40ml) under nitrogen at −78° C. After stirring at −78° for ½ hour, the mixture was stirred at 0° for 5 minutes.

(ii) Simultaneously with step a(i), a solution of redistilled 3,4-dihydroisoquinoline (5.24g; 0.04mol) in dry tetrahydrofuran (100ml) was cooled in an ice-bath under nitrogen, then treated dropwise with trimethylsilyl trifluoromethanesulphonate (8.50ml; 0.04mol). The mixture was stirred at 0° for ½ hour, then cooled to −78° C.

b) The ice-cold solution of step a(i) was pumped by nitrogen pressure through a transfer needle into the mixture of step a(ii). The mixture was stirred at −78° C. for 1 hour then at 0° C. for 2 hours, allowing the ice to melt and the mixture to come to room temperature. The mixture was decomposed by the addition of water and the organic solvents were evaporated in vacuo. The aqueous residue was diluted with dil. aq. $Na_2CO_3$ and extracted with dichloromethane (3×30 ml). The combined extracts were dried ($MgSO_4$), filtered and evaporated to give an oil (7.67g).

The oil was chromatographed on silica eluted with 2% ethanol-toluene. The product was eluted quickly as a maroon-red oil (6.6g), which was dissolved in hot isopropanol (20ml), treated with oxalic acid dihydrate (4.16;1 molar equivalent) and cooled. The crystals were collected by filtration and washed well with isopropanol and ether to give substantially pure 1-(2-furanyl)-1,2,3,4-tetrahydroisoquinoline, 1:1 ethanedioate (7.12g; 61.5%) as cream crystals.

An analytical sample was obtained by trituration of a portion of the product with hot methanol, then cooling and collecting the sample by filtration. After drying at 40°/1mm, the analytical sample had m.p. 224°–6° (dec; darkened above 180°)

Analysis: $C_{13}H_{13}NO \cdot (COOH)_2$ requires: C,62.3; H,5.2; N,4.8. Found: C,62.2: H,4.9; N,4.8%.

EXAMPLE 8

1RS, 2'SR-1-(2-Tetrahydrofuranyl)-1,2,3,4-tetrahydroisoquinoline

A solution of 1-(2-furyl)-1,2,3,4-tetrahydroisoquinoline (3.3g)(as prepared in Example 7) in ethanol (150ml) was treated with Adam's catalyst (1.5g) then hydrogenated at 50psi/room temperature for 5 hours, by which time uptake of hydrogen was complete. After filtration through kieselguhr, the solvent was evaporated to give a yellow gum (3.39g).

Chromatography on silica eluted with 2–10% ethanol in toluene gave (after two chromatographic separations) fractions containing substantially pure 1-(2-tetrahydrofuranyl)-1,2,3,4-tetrahydroisoquinoline as its 1RS, 2'SR-diastereoisomer (higher Rf in the eluant) (1.62g) and the 1RS, 2'RS diastereoisomer (lower Rf) (0.53g). Both isomers were oils.

The 1RS, 2'SR isomer was dissolved in hot isopropanol and treated with one molar equivalent of oxalic acid. Crystallisation occurred rapidly. After cooling, the crystals were collected by filtration, washed with cold isopropanol and dried at 40° C./1mm to give the 1:1 ethanedioate salt of the title compound, 1.75g mp 206°–209° (dec).

Analysis $C_{13}H_{17}NO \cdot (COOH)_2$ requires:C, 61.4;H, 6.5; N, 4.8. Found: C, 61.5; H,6.7; N,4.6%.

EXAMPLE 9

1RS, 2'RS-1-(2-Tetrahydrofuranyl)-1,2,3,4-tetrahydroisoquinoline

The 1RS, 2'RS diastereoisomer prepared as an oil in Example 8 was dissolved in hot isopropanol and treated with one molar equivalent of oxalic acid. Crystallisation occurred rapidly. After cooling, the crystals were collected by filtration, washed with cold isopropanol and dried at 40° C./1mm to give the 1:1 ethanedioate salt of the title compound, (0.46g) m.p. 164°–165° C.(dec).

Analysis: $C_{13}H_{17}NO \cdot (COOH)_2$ requires: C,61.4; H,6.5; N,4.8. Found: C,61.4; H,6.5; N,4.7%.

EXAMPLE 10

1RS, 2'SR-1-(2-Tetrahydrofuranyl)-2-methyl-1,2,3,4-tetrahydroisoquinoline

A solution of 1RS,2 SR-1-(tetrahydrofuran-2-yl)-1,2,3,4-tetrahydroisoquinoline, (0.89g; 4.38mmol) (prepared according to Example 8) in ethanol (50ml) was treated with 40% formaldehyde solution (2.5ml; large excess) and 5% palladium on charcoal (0.12g), then hydrogenated at atmospheric pressure for about 4.5 hours.

The mixture was filtered through kieselguhr, evaporated to dryness, and the residue taken up in hot ethanol (25ml), charcoaled and filtered while still hot. Evaporation gave a gum (0.68g) which was dissolved in hot ethanol (10ml), acidified with oxalic acid dihydrate (0.395g; 1 molar equiv) and cooled (ice). Scratching caused rapid precipitation. The crystals were collected by filtration and dried at 40°/1mm to give the title compound as the 1:1 ethanedioate salt (0.62g), m.p. 157°–161° (dec).

Analysis: $C_{14}H_{19}NO \cdot (COOH)_2$ requires:C,62.5; H,6.9; N,4.6. Found: C,62.6; H,7.2; N,4.3%.

EXAMPLE 11

1,2,3,4-Tetrahydro-1-(2-thienyl)isoquinoline a) A solution of 1.5m nBuLi in hexane (27ml; 0.04mol) was added dropwise to a cold (−78°), stirred solution of thiophene (3.20ml; 3.36g; 0.04mol) in dry tetrahydrofuran (40ml) under a nitrogen blanket. The solution was stirred at −78° C. for ½ hour, then warmed to 0° (ice-bath).

b) Simultaneously with (a), a solution of redistilled 3,4-dihydroisoquinoline (5.24g; 0.04 mol) in dry tetrahydrofuran (100ml) under nitrogen was cooled in an ice-bath then treated dropwise with trimethylsilyl triflate (8.50ml; 0.04mol). The mixture was stirred at 0° for ½ hour, then cooled to −78°.

c) The solution of step (a) at 0° was transferred by gentle nitrogen pressure into the product of step (b) at −78° C. When transfer complete, the mixture was stirred at −78° C. for 1 hour, then at room temperature for 2 hours. The mixture was decomposed by the addition of water (10ml) and the solvents were evaporated in vacuo The residue was taken up in dil, aq. $Na_2CO_3$ and extracted with dichloromethane (3×30ml). The combined extracts were dried ($MgSO_4$), filtered and evaporated to give a solid (8.74g) which was recrystallised from ethanol (10ml) to give 1,2,3,4-tetrahydro-1-(2-thienyl) isoquinoline (4.85g; 56.4%) as microneedles, m.p.113.5°-115.5°.

A sample (1.08g; 5mmol) of the above base was dissolved in hot ethanol (7ml), treated with maleic acid (0.58g; 5mmol) and cooled. Crystallisation occurred slowly to give, after filtration and drying at 40°/1mm, the 1:1 maleic acid salt of the title compound (1.15g), m.p. 150°-151°C.

Analysis: $C_{13}H_{13}NS$. $C_4H_4O_4$ requires: C,61.6; H,5.2; N,4.2. Found: C,61.4; H,5.1; N,4.1%.

EXAMPLE 12

1-(4-Hydroxyphenyl)-6,7-dihydroxy-1,2,3,4-tetrahydroisoquinoline

The preparation of the title compound via a Pictet Spengler condensation is described by Morita et al, in Agr. Biol. Chem., 39(2) 547-549, 1975. The compound had an $IC_{50}$ value of 0.48 μM in the procedure described hereinbefore for measuring GABA autoreceptor antagonism.

EXAMPLE 13

1-RS, 2'-SR-1-(2-Tetrahydrofuranyl)-2,2-dimethyl-1,2,3,4-tetrahydroisoquinolinium iodide -2-yl)-

A solution of 1RS. 2'-SR -1-(tetrahydrofuran-2-yl)-2-methyl-1,2,3,4-tetrahydroisoquinoline (0.5g, prepared according to Example 10) in ether (10 ml) was treated with methyl iodide (6 ml). The mixture was allowed to stand at room temperature overnight, then filtered giving a powder. The powder was triturated with ether (10 ml) collected by filtration and dried (35°/100 mm) to give the title compound (0.46g) mp 215°-8° C. (softens 210°)

Analysis: $C_{15}H_{22}NOI$ requires C,50.15; H,6.17; N,3.90. Found: C,50.55; H,6.19; N,3.84.

EXAMPLES 14-17

The following racemic compounds:

1 RS, 2'SR-1-(2-tetrahydrofuranyl)-1,2,3,4-tetrahydro-6,7-dimethoxyisoquinoline (Example 1)

1 RS, 2'SR-1-(2-tetrahydrofuranyl)-1,2,3,4-tetrahydroisoquinoline (Example 8)

were each resolved in the following manner:

To a hot solution of each in ethanol was added a hot solution of ½ molar equivalent of R(−)-3,5-dinitrobenzoyl-α-phenylglycine (a chiral resolving acid). The resulting solution was allowed to cool and stand for 1 hour. The resulting crystals, which were greatly enriched in one diastereoisomer (enantiomer and chiral agent), were collected by filtration and washed with cold ethanol.

The combined filtrate and washings were evaporated to dryness and basified with dil aq NaOH, extracted into $CH_2Cl_2$ and the combined extracts washed with water, dried (Mg $SO_4$) and evaporated. A hot solution of the resulting oil in ethanol was treated with a hot solution of 1 molar equivalent of S(+)-3,5-dinitrobenzoyl-o-phenylglycine and treated as before for the other diastereomer to give crystals greatly enriched in one diastereomer.

Both enriched solid diastereomeric salts were separately recrystallised from ethanol-water until each salt was diastereoisomerically pure with their respective resolving acid (approx 6 times). The salts were each converted to the enantiomeric bases (+or −) using dil aq NaOH, then extracted with $CH_2\ Cl_2$ and the combined extracts washed with water, dried ($MgSO_4$) and evaporated to give oils, then converted to organic salts and crystallised as the acid addition salts.

The optical rotations of the enantiomers of the compounds of Examples 1 and 8 were as follows:

| EXAMPLE NO | $[\alpha]_D^{23}$ (C = 1%. $H_2O$) | Melting Points |
|---|---|---|
| 14. (+) enantiomer of Example 1, maleate salt | +84° | 140-142°(dec) |
| 15. (−) enantiomer of Example 1, maleate salt | −83° | 142-143.5° |
| 16. (+) enantiomer of Example 8, maleate salt | +79° | 146-147.5° |
| 17. (−) enantiomer of Example 8, maleate salt | −78° | 147-150° |

EXAMPLES 18 AND 19

The (+) and (−) enantiomers of Examples 16 and 17 (free bases) were each N-methylated by reductive formylation using formaldehyde in ethanol and catalytic reduction with 5% Pd/C catalyst, at atmospheric pressure for 4½ hours, to give the (+) and (−) enantiomers of the corresponding N-methyl compounds, viz. (+)1R*,2'S*-1-(2-tetrahydrofuranyl)-2-methyl-1,2,3,4-tetrahydroisoquinoline, $[\alpha]_D^{23}$+39° and (−) 1R*,2'S*-1-(2-tetrahydrofuranyl)-2-methyl-1,2,3,4-tetrahydroisoquinoline, $[\alpha]_D^{23}$−28°

The (+) and (−) enantiomers were treated with oxalic acid to give the corresponding oxalate salts, mps 164-6 (dec) and 165-6 (dec) respectively.

EXAMPLE 20

1RS, 2'SR-(2-Tetrahydrofuranyl)-1,2,3,4-tetrahydro-6,7-methylenedioxyisoquinoline a) N-[2-(3,4-methylenedioxyphenyl)-ethyl]furan-2-carboxamide was prepared by condensation of 2-furoyl chloride and 3,4-methylenedioxyphenethylamine in dichloromethane with triethylamine as catalyst.

b) A solution of the amide from step a) (84g; 0.32 mol) in toluene (700ml) was added to phosphorus oxychloride (100g; 0.65 mol). The mixture was heated to reflux for 2 hours to give a precipitate in a solution. Evaporation of the solvents gave a residue which was recrystallised from ethyl acetate/methanol to give 1-(2-furanyl)-3,4-dihydro-6,7-methylene-dioxyisoquinoline hydrochloride (70g) as a powder.

c) The product of step b) was dissolved in water, basified with aq. $Na_2CO_3$ extracted with dichloromethane, dried ($MgSO_4$) and evaporated to give a solid (55g). This was dissolved in ethanol treated with 5% palladium on charcoal (30g) and hydrogenated at 100 psi/room temperature for 6 hours. Filtration and evaporation of the filtrate gave an oil (50g) which contained the two diastereoisomers of the product. The oil was dissolved in hot methanol (200 ml) and treated with a solution of one molar equivalent of maleic acid in methanol. Crystallisation occurred rapidly. The crystals were collected by filtration and recrystallised twice from methanol to give crystals of the maleate salt of the title compound, mp 198°-200° (dec).

Analysis: $C_{14}H_{17}NO_3 \cdot C_4H_4O_4$ requires: C,59.5; %,5.8; N,3.9. Found: C,59.5; H,5.8; N,3.8%.

EXAMPLE 21

1-(Furanyl)-2-methyl-1,2,3,4-tetrahydroisoquinoline a) 1-(Furan-2-yl)-3,4-dihydroisoquinoline was prepared by reacting phenethylamine with 2-furanoyl chloride followed by reflux with polyphosphoric acid.

b) To the product of step a) (30gm, 0.15 mol) in 100 ml $CHCl_3$ a large excess of methyl iodide was added and the solution stirred at room temperature for several hours.

The solution was poured into a large volume of ether with vigorous stirring to give the methiodide salt (42 gm) which was recrystallised from isopropanol/methanol.

c) Excess $NaBH_4$ was added portionwise to 59 gm of methiodide prepared according to step b) in refluxing isopropanol. After 2½ hours water was added followed by extraction with $CH_2Cl_2$. The extract was washed with water (twice), dried (Mg $SO_4$) and evaporated to leave a light brown oil (36 gm 97%). 2.1gm of this oil in hot isopropanol was treated with one equivalent of oxalic acid and diethyl ether was added causing the title compound to crystallise, mp 172°-4° C.

Analysis: $C_{14}H_{15}NO \cdot (COOH)_2$ requires: C,63.17; H,5.84; N,4.48. Found: C,63.36; H,5.65; N,4.62%.

EXAMPLE 22

1RS, 2′RS-1-(2-Tetrahydrofuranyl)-2-methyl-1,2,3,4-tetrahydroisoquinoline

To a suspension of sodium hydride 60% (100mg, 2,3,2mol) in THF (5ml) was added 1RS,2′RS-1-(2-tetrahydrofuranyl)-1,2,3,4-tetrahydroisoquinoline (500 mg, 2.46 mmol) in THF (3ml). The suspension was left at room temperature under nitrogen for 15 minutes. Methyl iodide (349mg 2,4,5 mmol) in THF (2ml) was added dropwise. The reaction was allowed to stir for 30 mins.

On completion of the reaction the solvent was evaporated and the oily solid partitioned between water (10ml) and diethyl ether (10ml). After a further ether extraction the organic solutions were combined and dried over sodium sulphate.

Subsequent column chromatography (DIPE, silica) of the 25 evaporated material yielded 226 mg (45%) of the title compound as an oil. The oil was converted to the oxalate salt and recrystallised (ethanol/ether) to yield a solid (95 mg) mp 121°-124° C.

Analysis: $C_{14}H_{19}NO \cdot (COOH)_2$ requires: C,59.89; H,7.07; N,4.37. Found C,59.99; H,7.36; N,4.12%.

We claim:

1. A method of treating anxiety, epilepsy, muscle spasms, sleep disorders, dyskinesia, depression and/or psychoses in an animal so afflicted which comprises administering to said animal so afflicted an effective amount of a compound having the formula

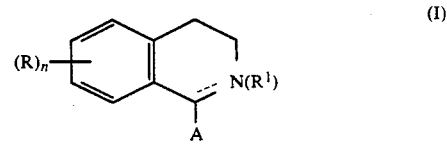

(I)

where
the dotted bond represents an optional double bond,
$(R)_n$ represents optional substitution on the benzene ring in one or more of the vacant ring positions by one or more substituents the same or different selected from lower alkyl, lower alkoxy, halogen, hydroxy, nitro, carboxy, lower alkylthio, SH, $NH_2$, or mono- or diloweralkylamino or $(R)_n$ represents disubstitution by an alkylenedioxy radical;
$R^1$ when present represents hydrogen, lower alkyl, aryl, or aryl lower alkyl, the aryl and aryl lower alkyl groups being optionally substituted by one or more substituents the same or different selected form hydroxy, halogen, lower alkyl, lower alkoxy, $NO_2$, CN, carboxy, lower alkylthio, SH, $NH_2$ and mono- or di-loweralkylamino or by alkylenedioxy;
$R^2$ represents hydrogen or lower alkyl;
and A represents aryl optionally substituted as for $R^1$ when aryl or a group of the formula

(Ia)

or

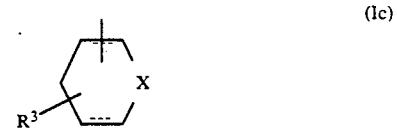

(Ic)

wherein the dotted lines represent optional bonds, X represents NH, oxygen, or sulphur and $R^3$ represents hydrogen or lower alkyl; or a pharmaceutically acceptable salt thereof which acts selectively as an antagonist of gamma amino butyric acid (GABA) at GABA autoreceptors relative to $GABA_A$ receptors provided that when $R^1$ is hydrogen and A represents an optionally substituted carbocyclic aryl, then $(R)_n$ is other than hydroxy or di-substitution by hydroxy or loweralkoxy.

2. A method as claimed in claim 1 in which (i) A represents formula Ia or Ic or (ii) A represents thienyl or furyl and $R^1$ is lower alkyl or optionally substituted aryl or aryl lower alkyl; or a pharmaceutically acceptable salt thereof.

3. A method as claimed in claim 1 in which A represents phenyl, pyridyl, furanyl, dihydrofuranyl, tetrahydrofuranyl, thienyl tetrahydrothienyl, pyranyl or tetrahydropyranyl and such groups substituted by methyl.

4. A method as claimed in claim 1 wherein A is 2-furanyl, 2-thienyl, 2-tetrahydrofuranyl or 2-tetrahydrothienyl.

5. A method as claimed claims 1 wherein $R^1$ is present and represents hydrogen, methyl, benzyl or p-chlorobenzyl.

6. A method according to claim 1 in which the compound of formula I is (+) or (−) 1RS, 2'SR-1-(2 -tetrahydrofuranyl) -1,2,3,4 - tetrahydro -6,7 -dimethoxyisoquinoline or a pharmaceutically acceptable salt thereof.

7. A method according to claim 1 in which the compound of formula I is 1RS, 2'RS-1-(2 -tetrahydrofuranyl) - 1,2,3,4 - tetrahydro -6,7 -dimethoxyisoquinoline or a pharmaceutically acceptable salt thereof.

8. A method according to claim 1 in which the compound of formula I is 1 - RS, 2'SR - 1 -(2-tetrahydrofuranyl) - 1,2,3,4 - tetrahydro-2 - methyl-6,7 - dimethoxyisoquinoline or a pharmaceutically acceptable salt thereof.

9. A method according to claim 1 in which the compound of formula I is 1-RS, 2'SR - 2 -benzyl-6,7-dimethoxy-1 - (2-tetrahydrofuranyl) - 1,2,3,4 -tetrahydroisoquinoline or a pharmaceutically acceptable salt thereof.

10. A method according to claim 1 in which the compound formula I is 1 - RS, 2'SR - 2 -(4-chlorobenzyl) -1-(2- tetrahydrofuranyl) -1,2,3,4 -tetrahydro-6,7 - dimethoxyisoquinoline or a pharmaceutically acceptable salt thereof.

11. A method according to claim 1 in which the compound of formula I is 1 - (2-furanyl) - 1,2,3,4 -tetrahydroisoquinoline or a pharmaceutically acceptable salt thereof.

12. A method according to claim 1 in which the compound of formula I is (+) or (−) 1 - RS, 2'SR -(2-tetrahydrofuranyl) -1,2,3,4 - tetrahydroisoquinoline or a pharmaceutically acceptable salt thereof.

13. A method to claim 1 in which the compound of formula I is 1 - RS, 2'RS - (2 - tetrahydrofuranyl)-1,2,3,4 - tetrahydroisoquinoline or a pharmaceutically acceptable salt thereof.

14. A method as claimed in claim 1 in which the compound of formula I is +) or (−) 1RS, 2'SR-1-(2-tetrahydrofuranyl) -2- methyl-1,2,3,4 -tetrahydroisoquinoline or a pharmaceutically acceptable salt thereof.

15. A method as claimed in claim 1 in which the compound of formula I is 1,2,3,4 - tetrahydro - 1 -(2 -thienyl) isoquinoline or a pharmaceutically acceptable salt thereof.

16. A method as claimed in claim 1 in which the compound of formula I is 1RS 2'SR-1-(2-tetrahydrofuranyl)-1,2,3,4-tetrahydro-6,7-methylenedioxyisoquinoline.

17. A method as claimed in claim 1 in which the compound of formula I is 1-(2-furanyl)-2-methyl-1,2,3,4-tetrahydroisoquinoline.

18. A pharmaceutical composition for treating anxiety, epilepsy, skeletal muscle spasm, sleep disorders, dyskinesia, depression, and/or psychoses comprising a compound of the formula

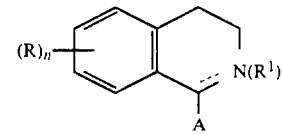

where
the dotted bond represents an optional double bond,
$(R)_n$ represents optional substitution on the benzene ring in one or more of the vacant ring positions by one or more substituents the same or different selected from lower alkyl, lower alkoxy, halogen, hydroxy, nitro, carboxy, lower alkylthio, SH, $NH_2$, or mono- or diloweralkylamino or $(R)_n$ represents disubstitution by an alkylenedioxy radical;

$R^1$ when present represents hydrogen, lower alkyl, aryl, or aryl lower alkyl, the aryl and aryl lower alkyl groups being optionally substituted by one or more substituents the same or different selected form hydroxy, halogen, lower alkyl, lower alkoxy, $NO_2$, CN, carboxy, lower alkylthio, SH, $NH_2$ and mono- or di-loweralkylamino or by alkylenedioxy;

$R^2$ represents hydrogen or lower alkyl;

and A represents thienyl, furanyl, or pyrrolyl optionally substituted as for $R^1$ or A represents a group of the formula

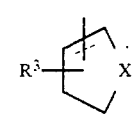

or

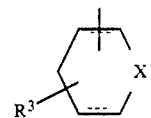

wherein the dotted lines represent optional bonds, X represents NH, oxygen, or sulphur and $R^3$ represents hydrogen or lower alkyl; or a pharmaceutically acceptable salt thereof and a pharmaceutically acceptable carrier provided that when $R^1$ is hydrogen or methyl or $R^1$ is absent A is not a substituted or unsubstituted 2-thienyl group, or 2-furanyl and when X is NH, $(R)_n$ is not 6,7-diloweralkoxy.

19. A composition as claimed in claim 18 in which the compound of formula I is 1-(2-furanyl)-2-methyl-1,2,3,4-tetrahydroisoquinoline.

20. A composition according to claim 18 in which the compound of formula I is 1-(2-furanyl)-1,2,3,4-tetrahydroisoquinoline or a pharmaceutically acceptable salt thereof.

21. A composition as claimed in claim 18 in which the compound of formula I is 1,2,3,4-tetrahydro-1-(2-thienyl) isoquinoline or a pharmaceutically acceptable salt thereof.

22. A compound having the formula

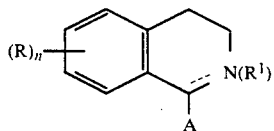

where
the dotted bond represents an optional double bond,
(R)$_n$ represents optional substitution on the benzene ring in one or more of the vacant ring positions by one or more substituents the same or different selected from lower alkyl, lower alkoxy, halogen, hydroxy, nitro, carboxy, lower alkylthio, SH, NH$_2$, or mono- or diloweralkylamino or (R)$_n$ represents disubstitution by an alkylenedioxy radical;

R$^1$ when present represents hydrogen, lower alkyl, aryl, or aryl lower alkyl, the aryl and aryl lower alkyl groups being optionally substituted by one or more substituents the same or different selected form hydroxy, halogen, lower alkyl, lower alkoxy, NO$_2$, CN, carboxy, lower alkylthio, SH, NH$_2$ and mono- or di-loweralkylamino or by alkylenedioxy;

R$_2$ represents hydrogen or lower alkyl;

and A represents thienyl, furanyl, or pyrrolyl optionally substituted as for R$^1$ or A represents a group of the formula

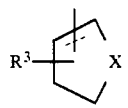

or

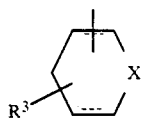

wherein the dotted lines represents optional bonds, X represents NH, oxygen, or sulphur and R$^3$ represents hydrogen or lower alkyl; or a pharmaceutically acceptable salt thereof; providing when R$^1$ is hydrogen or methyl or R$^1$ is absent A is not a substituted or unsubstituted 2-thienyl group, or 2furanyl and when X is NH, (R)$_n$ is not 6,7-diloweralkoxy.

23. A compound as claimed in claim 22 which A represents furanyl, dihydrofuranyl, tetrahydrofuranyl, thienyl tetrahydrothienyl, pyranyl or tetrahydropyranyl and such groups substituted by methyl.

24. A compound as claimed in claim 22 wherein A is 2-furanyl, 2-thienyl, 2-tetrahydrofuranyl or 2-tetrahydrothienyl.

25. A compound according to claim 22 which is (+) or (−) 1RS, 2'SR-1-(2 - tetrahydrofuran)-1,2,3,4-tetrahydro-6,7 - dimethoxyisoquinoline or a pharmaceutically acceptable salt thereof.

26. A compound according to claim 22 in which is 1RS, 2'RS-1-(2 - tetrahydrofuranyl) - 1,2,3,4 - tetrahydro-6,7 - dimethoxyisoquinoline or a pharmaceutically acceptable salt thereof.

27. A compound according to claim 22 which is 1 - RS, 2'SR - 1 -(2 -tetrahydrofuranyl) - 1,2,3,4 -tetrahydro-2 - methyl - 6,7 - dimethoxyisoquinoline or a pharmaceutically acceptable salt thereof.

28. A compound according to claim 22 which is 1-RS, 2'SR - 2 -benzyl - 6,7 - dimethoxy - 1 -(2-tetrahydrofuranyl) - 1,2,3,4 -tetrahydroisoquinoline or a pharmaceutically acceptable salt thereof.

29. A compound according to claim 22 which is 1 - RS, 2'SR - 2 - (4-chlorobenzyl) -1-(2- tetrahydrofuranyl)-1,2,3,4 - tetrahydro - 6,7 - dimethoxyisoquinoline or a pharmaceutically acceptable salt thereof.

30. A compound according to claim 22 which is (+) or (−) 1 - RS, 2'SR - (2-tetrahydrofuranyl) -1,2,3,4 -tetrahydroisoquinoline or a pharmaceutically acceptable salt thereof.

31. A compound according to claim 22 which is 1 - RS, 2'RS - (2 -tetrahydrofuranyl) -1,2,3,4 -tetrahydroisoquinoline or a pharmaceutically acceptable salt thereof.

32. A compound as claimed in claim 22 which is (+) or (−) 1RS, 2'SR-1- (2-tetrahydrofuranyl) -2-methyl-1,2,3,4 - tetrahydroisoquinoline or a pharmaceutically acceptable salt thereof.

33. A compound as claimed in claim 22 which is 1RS, 2'SR-1-(2-tetrahydrofuranyl)-1,2,3,4-tetrahydro-6,7-methylenedioxyisoquinoline.

* * * * *